(12) United States Patent
Mizumoto et al.

(10) Patent No.: US 8,778,267 B2
(45) Date of Patent: Jul. 15, 2014

(54) ANALYZER

(75) Inventors: Toru Mizumoto, Kobe (JP); Keisuke Tsutsumida, Kobe (JP)

(73) Assignee: Sysmex Corporation, Kobe (JP)

( * ) Notice: Subject to any disclaimer, the term of this patent is extended or adjusted under 35 U.S.C. 154(b) by 1137 days.

(21) Appl. No.: 12/268,852

(22) Filed: Nov. 11, 2008

(65) Prior Publication Data

US 2009/0125271 A1 May 14, 2009

(30) Foreign Application Priority Data

Nov. 12, 2007 (JP) ................................. 2007-292693

(51) Int. Cl.
*G01N 35/08* (2006.01)
*G06F 9/445* (2006.01)
*G01N 35/00* (2006.01)
*G06F 9/44* (2006.01)

(52) U.S. Cl.
CPC ........ *G01N 35/00584* (2013.01); *G06F 9/4448* (2013.01); *G01N 35/00871* (2013.01)
USPC .................... 422/67; 422/73; 700/266; 704/8

(58) Field of Classification Search
None
See application file for complete search history.

(56) References Cited

U.S. PATENT DOCUMENTS 7,013,260 B2   3/2006  Asada
2002/0010806 A1*  1/2002  Yamade ........................ 709/327
2007/0231208 A1  10/2007  Tanaka et al.

FOREIGN PATENT DOCUMENTS

| JP | 05-072212 A | 3/1993 |
| JP | 2002-350451 A | 12/2002 |
| JP | 2002-351591 A | 12/2002 |
| JP | 2007-271433 A | 10/2007 |

* cited by examiner

*Primary Examiner* — P. Kathryn Wright
(74) *Attorney, Agent, or Firm* — Sughrue Mion, PLLC

(57) ABSTRACT

An analyzer includes a second memory enabled to memorize that control by a controller is for first area, the controller controls at least one of measurement, analysis and display to be for a first area when a second application program starts in a case where said second memory memorizes that the control by the controller is for the first area.

17 Claims, 9 Drawing Sheets

ANALYZER

BACKGROUND OF THE INVENTION

1. Field of the Invention

The present invention relates to an analyzer and a method of restricting a function of an application program in an analyzer, and more particularly, it relates to an analyzer capable of functioning in specifications different for respective areas and a method of restricting a function of an application program in such an analyzer.

2. Description of the Background Art

An analyzer capable of functioning in specifications different for respective area is known in general, as disclosed in U.S. Pat. No. 7,013,260, for example.

The aforementioned U.S. Pat. No. 7,013,260 discloses a sample analyzer allowing display by using a language for an area which a user demands.

The analyzers have heretofore used in a plurality of areas, and only the analyzer used in a prescribed area among the plurality of areas is often provided with an additional function performing particular control. In this case, an application program for the prescribed area different from an application program for other areas is generally installed into the analyzer used in the prescribed area to perform the particular control for the prescribed area.

In the use of the aforementioned sample analyzer described in U.S. Pat. No. 7,013,260 in the prescribed area, however, in a case where the application program for the prescribed area for performing the particular control for the prescribed area is installed into the sample analyzer, and the user hereafter installs the application program for other areas into the sample analyzer, the sample analyzer disadvantageously performs control for other areas when the user stars the application program for other areas. In other words, the sample analyzer disadvantageously does not perform the particular control for the prescribed area although used in the prescribed area, once the application program for other areas starts.

SUMMARY OF THE INVENTION

The scope of the present invention is defined solely by the appended claims, and is not affected to any degree by the statements within this summary.

A first aspect of the present invention is an analyzer, comprising: a measurement section for measuring a specimen and acquiring measurement data; a controller, including a first memory under control of a processor, the first memory storing instructions enabling the processor to carry out operations, comprising: analyzing the measurement data acquired by the measurement section and acquiring results of analysis; displaying the results of analysis acquired; and controlling at least one of measurement, analysis and display to be for a first area when a first application program for the first area starts, while controlling at least one of the measurement, the analysis and the display to be for a second area when a second application program for the second area starts; and a second memory enabled to memorize that the control by the controller is for the first area, wherein the controller controls at least one of the measurement, the analysis and the display to be for the first area when the second application program starts in a case where the second memory memorizes that the control by the controller is for the first area.

A second aspect of the present invention is an analyzer comprising: installation accepting means for accepting installation of a first application program and a second application program acquiring results of analysis of specimen, wherein the first application program is for a first area and the second application program is for a second area; execution means for executing the first application program and the second application program; and restriction means for restricting at least a partial function of the second application program, when the installation accepting means accepts the installation of the first application program and the execution means thereafter executes the second application program.

A third aspect of the present invention is a method of restricting a function of an application program in an analyzer, comprising steps of: accepting installation of a first application program acquiring results of analysis of specimen, wherein the first application program is for a first area; accepting installation of a second application program acquiring the results of analysis of the specimen, wherein the second application program is for a second area; executing the second application program; and restricting at least a partial function of the second application program in a case where the installation of the first application program has been accepted.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

The preferred embodiments of the present invention will be described hereinafter with reference to the drawings.

A urinary particle analyzer 1 according to an embodiment of the present invention will be now described with reference to FIGS. 1 to 4.

Figure 1:
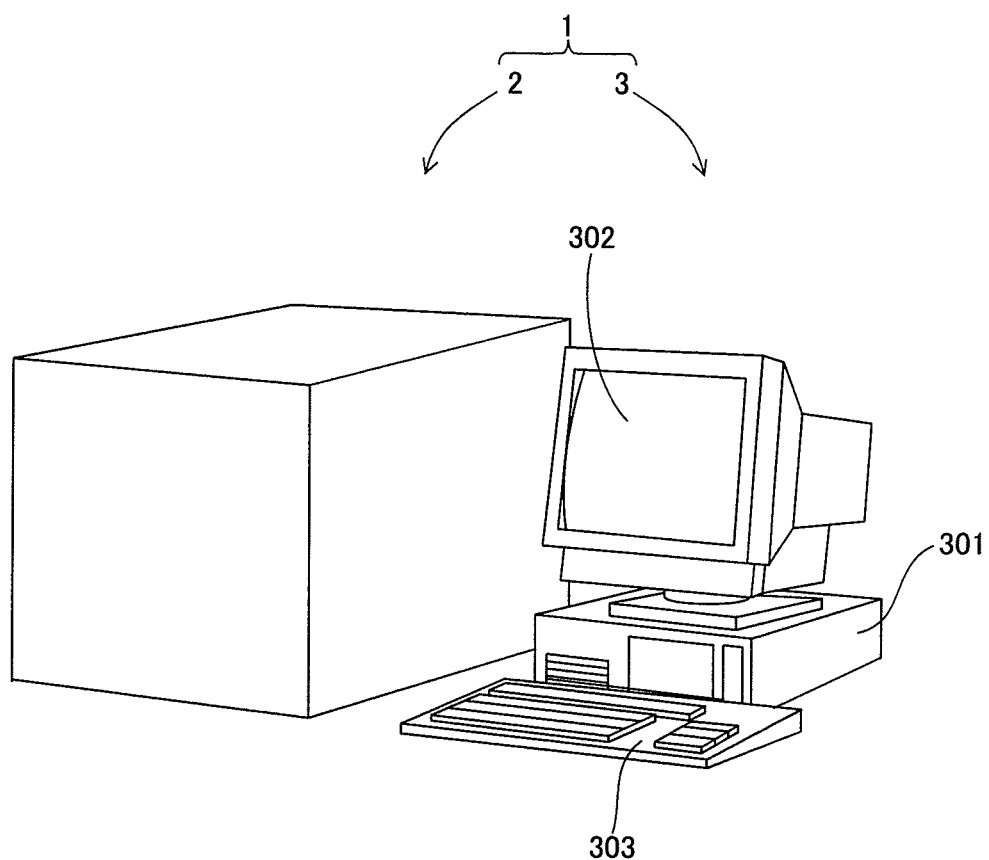
FIG. 1 is a perspective view showing a urinary particle analyzer according to an embodiment of the present invention.

The urinary particle analyzer 1 according to the embodiment of the present invention is constituted by a measuring apparatus 2 optically measuring particles contained in urine by a flow cytometer and a control apparatus 3 processing a measurement value output from the measuring apparatus 2 to obtain the results of analysis, as shown in FIG. 1.

Figure 2:
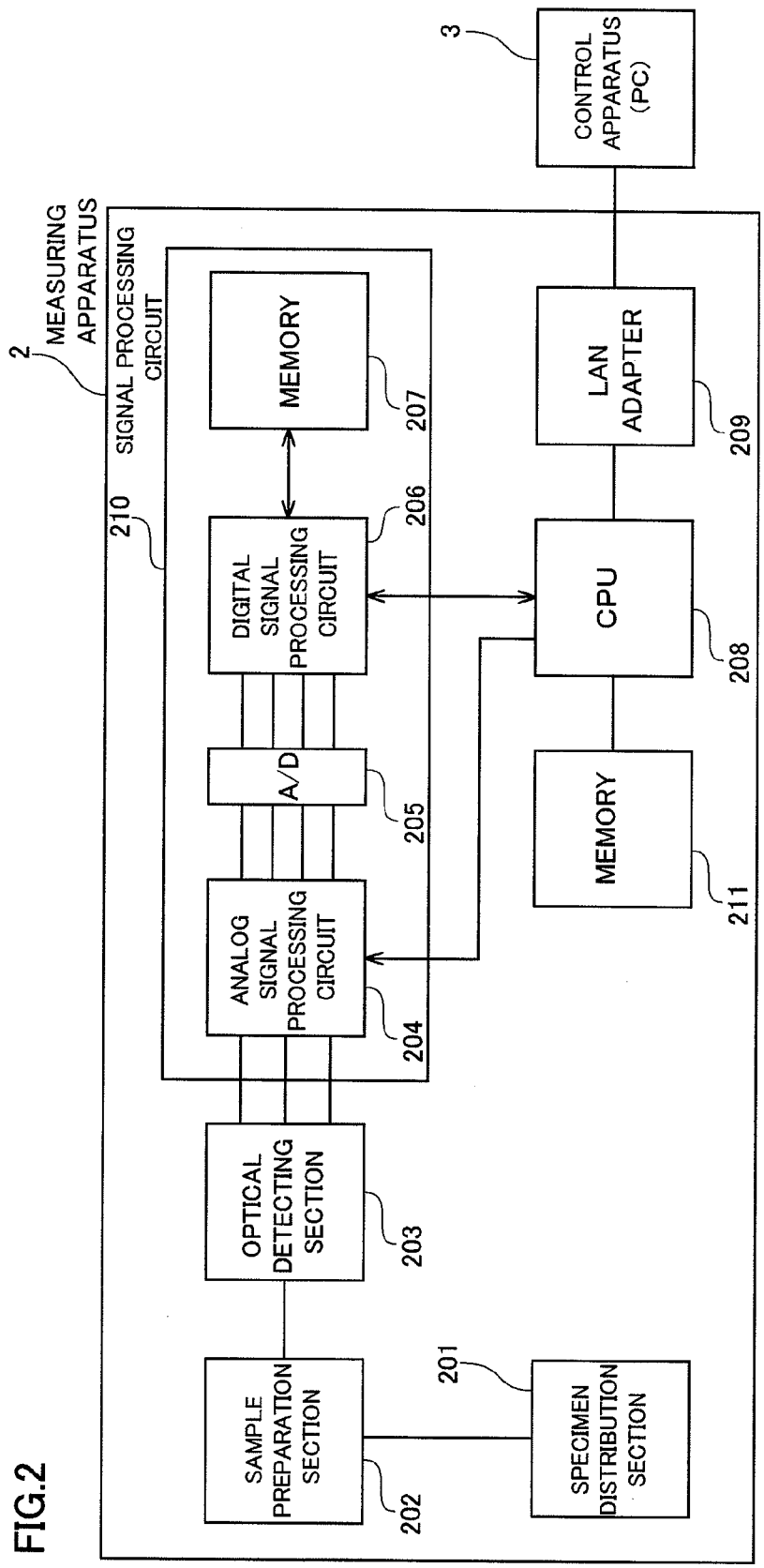
FIG. 2 is a block diagram showing the structure of a measuring apparatus of the urinary particle analyzer according to the embodiment shown in FIG. 1.

As shown in FIG. 2, the measuring apparatus 2 is provided with a specimen distribution section 201, a sample preparation section 202, and an optical detecting section 203, an analog signal processing circuit 204 for executing amplification of output by the optical detecting section 203 and filter processing, an A/D converter 205 for converting output of the analog signal processing circuit 204 to digital signals and a digital signal processing circuit 206 for executing a predetermined waveform processing for digital signals. Further, the measuring apparatus 2 is provided with a memory 207 connected to the digital signal processing circuit 206, a CPU 208 connected to the analog signal processing circuit 204 and the digital signal processing circuit 206 and a LAN adapter 209 connected to the CPU 208. The control apparatus 3 is LAN connected to the measuring apparatus 2 through the LAN adapter 209. The analog signal processing circuit 204, the A/D converter 205, the digital signal processing circuit 206 and the memory 207 constitutes a signal processing circuit 210 for electric signals being output by the optical detecting section 203. The measuring apparatus 2 is provided with a memory 211 such as a BBURAM (battery backup RAM) connected to the CPU 208, and the like.

The specimen distribution section 201 is so formed that a prescribed distributed quantity of urine (specimen) is dispensed to the sample preparation section 202. The sample preparation section 202 is so formed as to prepare a measurement sample from the urine (specimen) dispensed by the specimen distribution section 201 and a reagent and supply the prepared measurement sample to a sheath flow cell 203c (see FIG. 3), described later, of the optical detecting section 203 together with sheath fluid.

Figure 3:
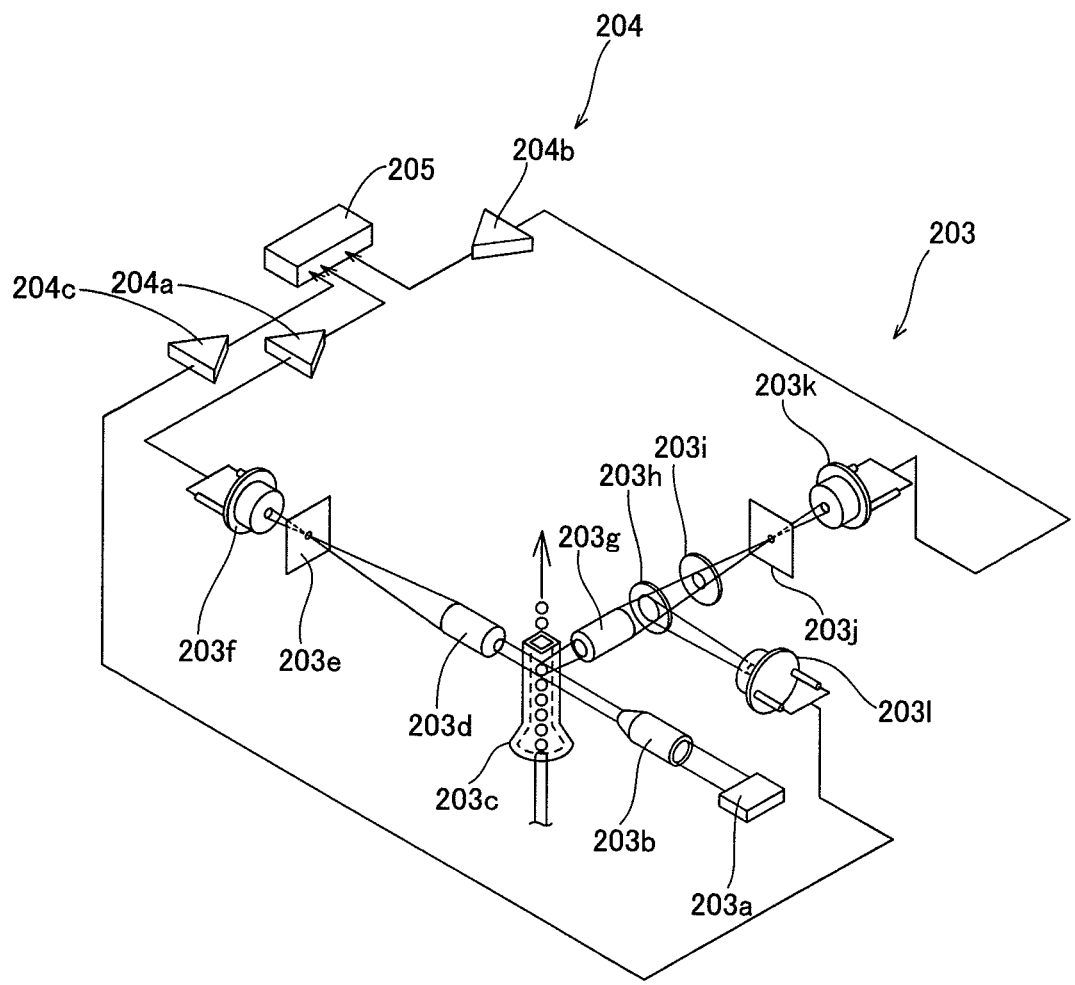
FIG. 3 is a diagram for illustrating the structure of an optical detecting section of the measuring apparatus of the urinary particle analyzer according to the embodiment shown in FIG. 1.

As shown in FIG. 3, the optical detecting section 203 includes a light emitting section 203a for emitting a laser beam, an illumination lens unit 203b, a sheath flow cell 203c for applying the laser beam, a condensing lens 203d, a pinhole 203e and a PD (photodiode) 203f arranged on an extension line of a traveling direction of the laser beam emitted from the light emitting section 203a, a condensing lens 203g, a dichroic mirror 203h, an optical filter 203i, a pinhole plate 203j having a pinhole and a PMT (Photomultiplier) 203k arranged in a direction intersecting with the traveling direction of the laser beam emitted from the light emitting section 203a, and a PD 203l arranged in a lateral direction of the dichroic mirror 203h.

The light emitting section 203a is provided for emitting light with respect to the flow of the sample including the measurement sample passing through the inside of the sheath flow cell 203c. The illumination lens unit 203b is provided for parallelizing the light applied from the light emitting section 203a. The PD 203f is provided for receiving forward scattered light emitted from the sheath flow cell 203c.

The dichroic mirror 203h is provided for separating side scattered light and side fluorescence emitted from the sheath flow cell 203c. More specifically, the dichroic mirror 203h is provided for introducing the side scattered light emitted from the sheath flow cell 203c into the PD 203l and introducing the side fluorescence emitted from the sheath flow cell 203c to the PMT 203k. The PD 203l is provided for receiving the side scattered light. The PMT 203k is provided for receiving the side fluorescence. The PDs 203f and 203l and the PMT 203k have functions of converting the received light signals to electric signals respectively.

As shown in FIG. 3, the analog signal processing circuit 204 includes amplifiers 204a, 204b and 204c. The amplifiers 204a, 204b and 204c are provided for executing amplification and waveform processing for the electric signals output from the PDs 203f and 203l and PMT 203k respectively.

The memory 211 is so formed as to store information (determination result information) indicating whether or not a replaced new reagent is a dedicated reagent (genuine product). More specifically, a CPU 301a, described later, of the control apparatus 3 determines whether or not the newly replaced reagent is the dedicated reagent, and the memory 211 is so formed as to store the determination result information based on the results of the determination.

Figure 4:
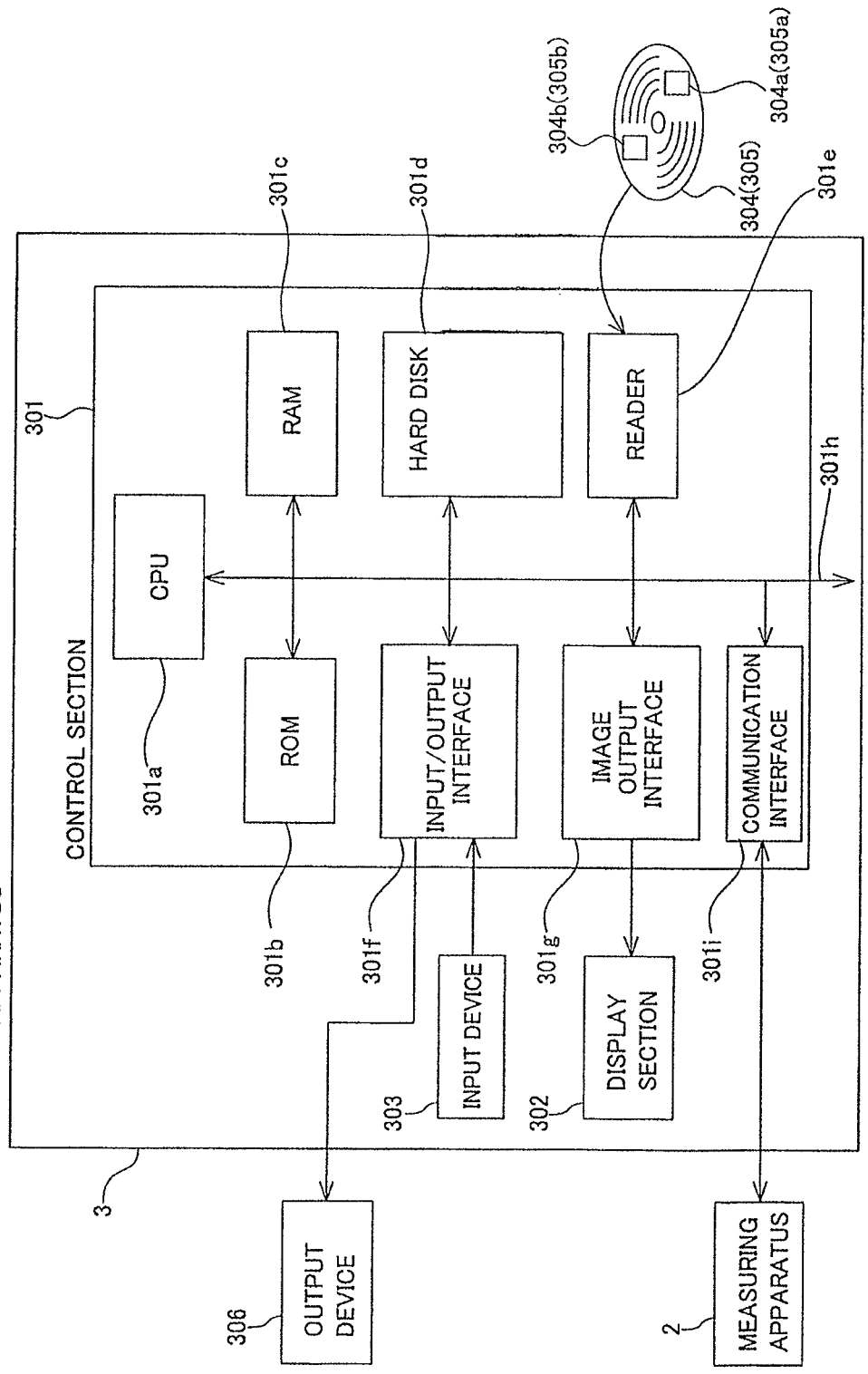
FIG. 4 is a block diagram showing the structure of a control apparatus of the urinary particle analyzer according to the embodiment shown in FIG. 1.

As shown in FIG. 1, the control apparatus 3 is formed by a personal computer (PC) or the like. The control apparatus 3 includes a control section 301, a display section 302 and an input device 303. The control apparatus 3 has a function of accepting an operation of the user, transmitting an instruction to the measuring apparatus 2, receiving measurement data (measurement value) from the measuring apparatus 2 and processing the measurement data to display results of analysis. As shown in FIG. 4, the control section 301 is constituted by the CPU 301a, a ROM 301b, a RAM 301c, a hard disk 301d, a reader 301e, an input/output interface 301f, an image output interface 301g and a communication interface 301i. The CPU 301a, the ROM 301b, the RAM 301c, the hard disk 301d, the reader 301e, the input/output interface 301f, the image output interface 301g and the communication interface 301i are connected by a bus 301h.

The CPU 301a is provided for executing computer programs recorded in the ROM 301b and computer programs loaded in the RAM 301c. The ROM 301b may be a mask ROM, a PROM, an EPROM, an EEPROM or the like, which stores computer programs executed by the CPU 301a and data used by these computer programs. Further, the CPU 301a has a function of processing the measurement value measured by the measuring apparatus 2 to obtain results of analysis and outputting an image signal corresponding to an analytical result screen 500 (see FIG. 11) for displaying the results of analysis to the image output interface 301g.

When the user replaces a reagent used in the measuring apparatus 2, the CPU 301a outputs the image signal to the image output interface 301g so as to display a reagent replacement screen (not shown) on the display section 302. This reagent replacement screen is so formed that the user can input a unique reagent code of 27 characters attached to a reagent container (not shown). The reagent code is an encrypted reagent code of 27 characters for storing unique information such as a lot number for acquiring expiration date or traceability in the dedicated reagent (genuine product) adequate for measurement by the measuring apparatus 2. This reagent code is encrypted using a hash function such as MD (message digest algorithm) 5 and is so formed that the CPU 301a is capable of determining whether or not the replaced reagent is the dedicated reagent (genuine product) adequate for use in the measuring apparatus 2 on the bases of the encrypted alphanumeric characters of 27 characters.

The CPU 301a is so formed as to measure the residual quantity of a reagent in use and store the information of the residual quantity in the hard disk 301d together with the reagent code of the reagent. The hard disk 301d is capable of storing the reagent codes and the information of the residual quantity of a plurality of reagents which have been used in the past as a reagent replacement history. Further, the CPU 301a is so formed as to determine whether or not the replaced new reagent is the dedicated reagent (genuine product) on the basis of both of the reagent code and the residual quantity.

The RAM 301c is constituted by an SRAM or a DRAM. The RAM 301c is employed for reading the computer programs recorded in the ROM 301b and the hard disk 301d. Further, the RAM 301c is utilized as a working area of the CPU 301a when executing these computer programs.

An operating system and various computer programs such as application programs to be executed by the CPU 301a as well as data employed for executing the computer programs are installed in the hard disk 301d. An application program 304a or 305a, described later, is also installed in this hard disk 301d.

The reader 301e is formed by a flexible disk drive, a CD-ROM drive or a DVD-ROM drive, and can read computer programs or data recorded in portable recording mediums 304 and 305. The portable recording medium 304 stores the application program 304a for making the computer achieve a prescribed function and an installation program 304b for installing the application program 304a in the computer. Similarly to the portable recording medium 304, the portable recording medium 305 stores the application program 305a for making the computer achieve a prescribed function and an installation program 305b for installing the application program 305a in the computer. When the installation program 304b is started, the computer employed as the control apparatus 3 can read the application program 304a from the portable recording medium 304 and install the application program 304a in the hard disk 301d. The portable recording medium 305 is formed similarly to the portable recording medium 304. The portable recording medium 304 is provided for country A, and the portable recording medium 305 is provided for countries (country B, country C and country D, for example) other than country A. According to this embodiment, the application program 304a stored in the portable recording medium 304 and the application program 305a stored in the portable recording medium 305 are substantially the same application program. Each application program includes a program making the control apparatus 3 execute control for country A and control for the countries (country B, country C and country D, for example) other than country A. More specifically, each of the application programs 304a and 305a includes a specimen analysis program for transmitting a measurement start signal, analyzing a received measurement value and displaying the results of analysis and a restriction program for restricting a partial function of the specimen analysis program. The specimen analysis program normally makes the control apparatus 3 execute the control for the countries other than country A while making the control apparatus 3 execute the control for country A when the control program restricts the partial function of the specimen analysis program.

The aforementioned application programs 304a and 305a are provided not only by the portable recording mediums 304 and 305 respectively, but can be provided also from an external apparatus communicably connected with the computer by an electric communication line (whether wire or wireless) through the aforementioned electric communication line. For example, it is also possible that the aforementioned application program 304a or 305a is stored in a hard disk of a server computer on the Internet, so that the computer accesses this server computer, downloads the application program 304a or 305a and installs the same in the hard disk 301d.

Further, the operating system such as Windows (registered trademark) manufactured and sold by Microsoft, U.S.A., providing graphical user interface environment is installed in the hard disk 301d. In the following description, it is assumed that the application programs 304a and 305a according to this embodiment operate on the aforementioned operating system.

The output interface 301f is constituted by a serial interface such as USB, IEEE 1394 or RS-232C, a parallel interface such as SCSI, IDE or IEEE 1284, an analog interface formed by a D/A converter, an A/D converter etc. or the like, for example. The input device 303 including a keyboard and a mouse is connected to the input/output interface 301f, so that the user can input data into the control apparatus 3 by using the input device 303. An output device 306 including a printer and the like is connected to the input/output interface 301f.

The communication interface 301i is Ethernet (registered trademark) interface, and a data processing apparatus 3 is capable of transmitting and receiving data to and from the measuring apparatus 2 connected by a LAN cable using a prescribed communication protocol (TCP/IP) by means of this communication interface 301i.

The image output interface 301g is connected to the display section 302 formed by an LCD, CRT or the like, so that an image signal received from the CPU 301a is output to the display section 302. The display section 302 displays images (screens) in accordance with the input image signal.

In the urinary particle analyzer 1 according to the embodiment of the present invention, an operation for installing the application program 304a from the portable recording medium 304 for country A will be now described with reference to FIGS. 4 and 5.

Figure 5:
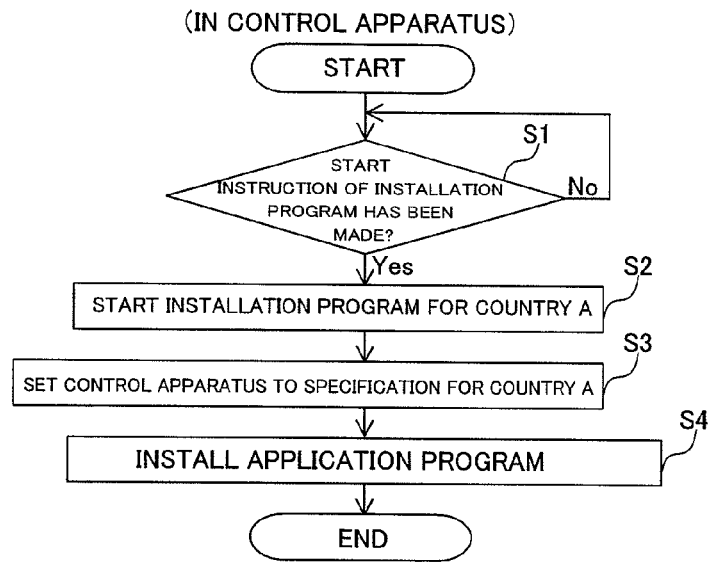
FIG. 5 is a flow chart for illustrating an operation for installing an application program from a portable recording medium for country A in the urinary particle analyzer according to the embodiment shown in FIG. 1.

At a step S1 in FIG. 5, the portable recording medium 304 is set in the reader 301e (see FIG. 4) of the control apparatus 3 and the CPU 301a thereafter determines whether or not the user has started the installation program 304b. This determination is repeated when no start instruction by the user is made, while the installation program 304b is started at a step S2 when the start instruction is made. The installation program 304b may be so formed as to be automatically started with no instruction by the user when the reader 301e reads the contents of the portable recording medium 304. Then the control apparatus 3 is automatically set to a specification for country A at a step S3, and the application program 304a is installed into the hard disk 301d at a step S4. Thus, when the user instructs the start of the application program 304a, the application program 304a is started in a state where the control apparatus 3 is set to the specification of the country A. According to this embodiment, specifications for country B, country C and country D are indicated as described later in addition to the aforementioned specification for country A, and layouts of the analytical result screens or output formats of the respective specifications are different from each other so as to correspond to laws or customs of the respective countries. The urinary particle analyzer 1 according to this embodiment is so formed that the user can select a preferable display language from a plurality of languages such as Japanese, English and Chinese. Even when any specification described above has been set, the user can select any display language. Thereafter the operation is ended.

In the urinary particle analyzer 1 according to the embodiment of the present invention, an operation for installing the application program 305a from the portable recording medium 305 for the countries other than country A will be now described with reference to FIGS. 4 and 6.

Figure 6:
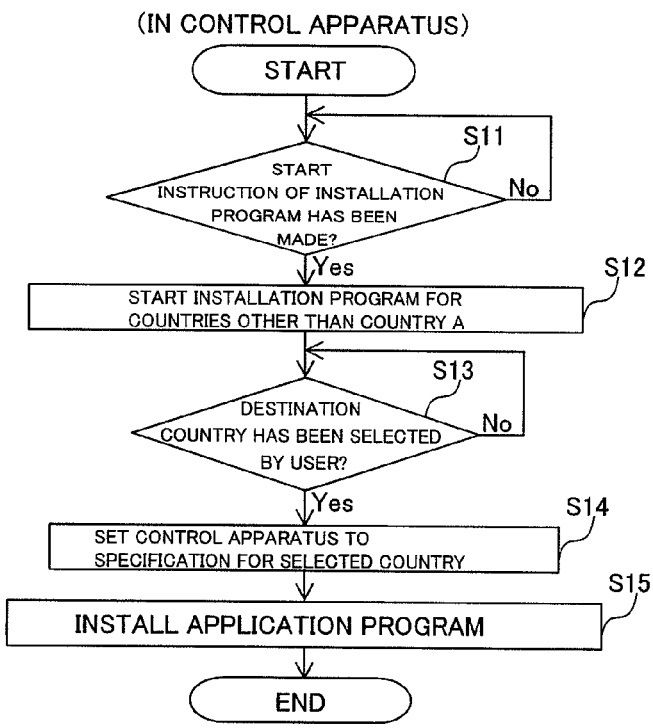
FIG. 6 is a flow chart for illustrating an operation for installing an application program from a portable recording medium for countries other than country A in the urinary particle analyzer according to the embodiment shown in FIG. 1.

At a step S11 in FIG. 6, the portable recording medium 305 is first set in the reader 301e (see FIG. 4) of the control apparatus 3 and the CPU 301a thereafter determines whether or not the user has started the installation program 305b. This determination is repeated when no start instruction by the user is made, while the installation program 305b is started at a step S12 when the start instruction is made. Then the CPU 301a determines whether or not the user has selected a destination country at a step S13. At this time, when the installation program 305b for countries other than country A is started, the user can select the destination country from a destination country selection screen (not shown) so as to set the control apparatus 3 to a specification for any one of country B, country C and country D other than country A.

The determination of the step S13 is repeated until the user selects the destination country. When the user selects the destination country, the control apparatus 3 is set to a specification for the selected country at a step S14, and the application program 305a is installed into the hard disk 301d at a step S15. Thus, when the user instructs the start of the installed application program 305a, the application program 305a is started in a state where the control apparatus 3 is set to the specification for the country selected by the user. Thereafter the operation is ended.

In the urinary particle analyzer 1 according to the embodiment of the present invention, an update operation of a genuine product flag for updating the information as to whether or not a reagent is a genuine product will be now described with reference to FIGS. 2, 4 and 7.

Figure 7:
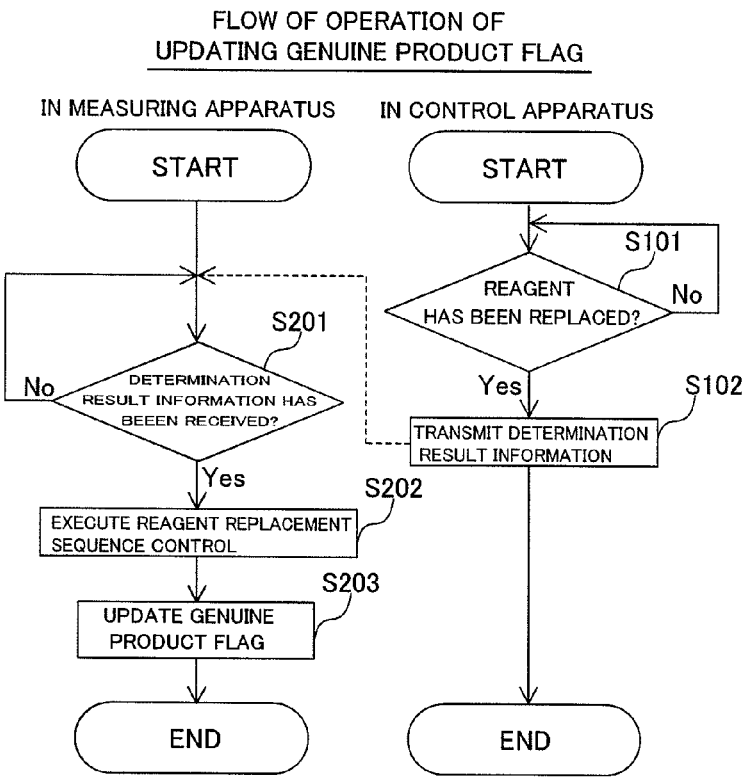
FIG. 7 is a flow chart for illustrating an operation of updating information as to whether or not a reagent is a genuine product in the urinary particle analyzer according to the embodiment shown in FIG. 1.

In the control apparatus 3, it is determined whether or not the reagent has been replaced at a step S101 in FIG. 7, and this determination is repeated when the reagent is not replaced. When the reagent is replaced, a signal of the determination result information obtained by determining whether or not the replaced reagent is the genuine product is transmitted to the measuring apparatus 2 at a step S102 and the operation is ended. As to whether or not the replaced reagent is the genuine product, the CPU 301a (see FIG. 4) determines it on the bases of the reagent code unique to each reagent input when replaced.

In the measuring apparatus 2, on the other hand, a signal of the determination result information transmitted from the control apparatus 3 is received at a step S201. Then, sequence control in reagent replacement is executed at a step S202. This sequence control in the reagent replacement is a preparatory operation for performing the next measurement. More specifically, when the reagent is replaced, air is leaked into a tube through which the reagent flows or no reagent exists in the space of the tube where the reagent should normally exist. In order to prevent this situation, the reagent is sucked from a newly set reagent container into the tube so that the reagent fills up the tube in the sequence control in reagent replacement.

At a step S203, the memory 211 (see FIG. 2) stores information as to whether or not the replaced reagent is the dedicated reagent (genuine product) on the basis of the received signal of the determination result information. More specifically, the genuine product flag stored in the memory 211 is updated to be turned on when the replaced reagent is the dedicated reagent (genuine product), while the genuine product flag is updated to be turned off when the replaced reagent is a nondedicated reagent (non-genuine product). Thereafter, the operation of the measuring apparatus 2 is ended.

In the urinary particle analyzer 1 according to the embodiment of the present invention, an operation of displaying a warning message when the nondedicated reagent is employed will be now described with reference to FIGS. 2, 4, 8 and 9.

Figure 8:
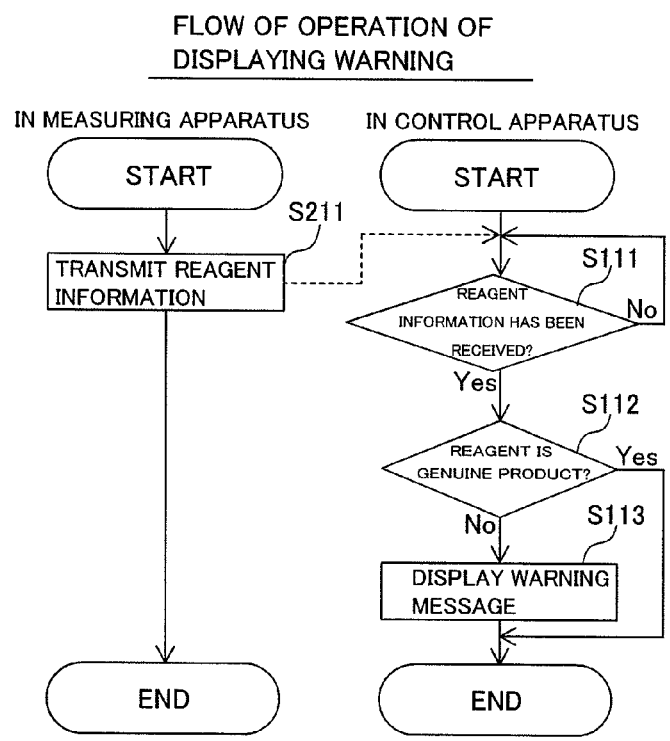
FIG. 8 is a flow chart for illustrating an operation of displaying a warning message in a case where a nondedicated reagent is used in the urinary particle analyzer according to the embodiment shown in FIG. 1.

First, a reagent information signal is transmitted to the control apparatus 3 on the basis of a state of the genuine product flag stored in the memory 211 (see FIG. 2) of the measuring apparatus 2 at a step S211 in FIG. 8. More specifically, the control apparatus 3 receives a signal indicating that the reagent to be used is the dedicated reagent (genuine product) when the genuine product flag is in an ON-state, while the control apparatus 3 receives a signal indicating that the reagent to be used is the nondedicated reagent (non-genuine product) and the operation is ended when the genuine product flag is in an OFF-state.

Figure 9:
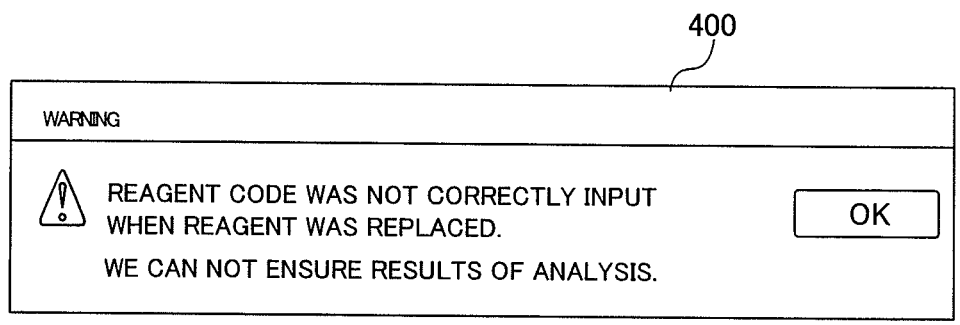
FIG. 9 is a diagram showing a warning screen of the urinary particle analyzer according to the embodiment shown in FIG. 1.

In the control apparatus 3, the reagent information signal transmitted from the measuring apparatus 2 is received at a step S111, and the CPU 301a (see FIG. 4) confirms whether or not the reagent to be used is the dedicated reagent (genuine product) on the basis of the received reagent information signal at a step S112. While the operation is ended when the reagent to be used is the dedicated reagent (genuine product), a warning screen 400 is displayed at a step S113 as shown in FIG. 9 when the reagent to be used is the nondedicated reagent (non-genuine product). In the warning screen 400, the warning indicating that the reagent code is not correctly input when the reagent is replaced and the results of analysis can not be ensured is displayed. Thereafter an operation of the control apparatus 3 is ended. This operation is performed when the urinary particle analyzer 1 starts.

Operations of start, measurement and analysis of the urinary particle analyzer 1 according to the embodiment of the present invention will be now described with reference to FIGS. 2, 4, 10 and 11.

Figure 10:
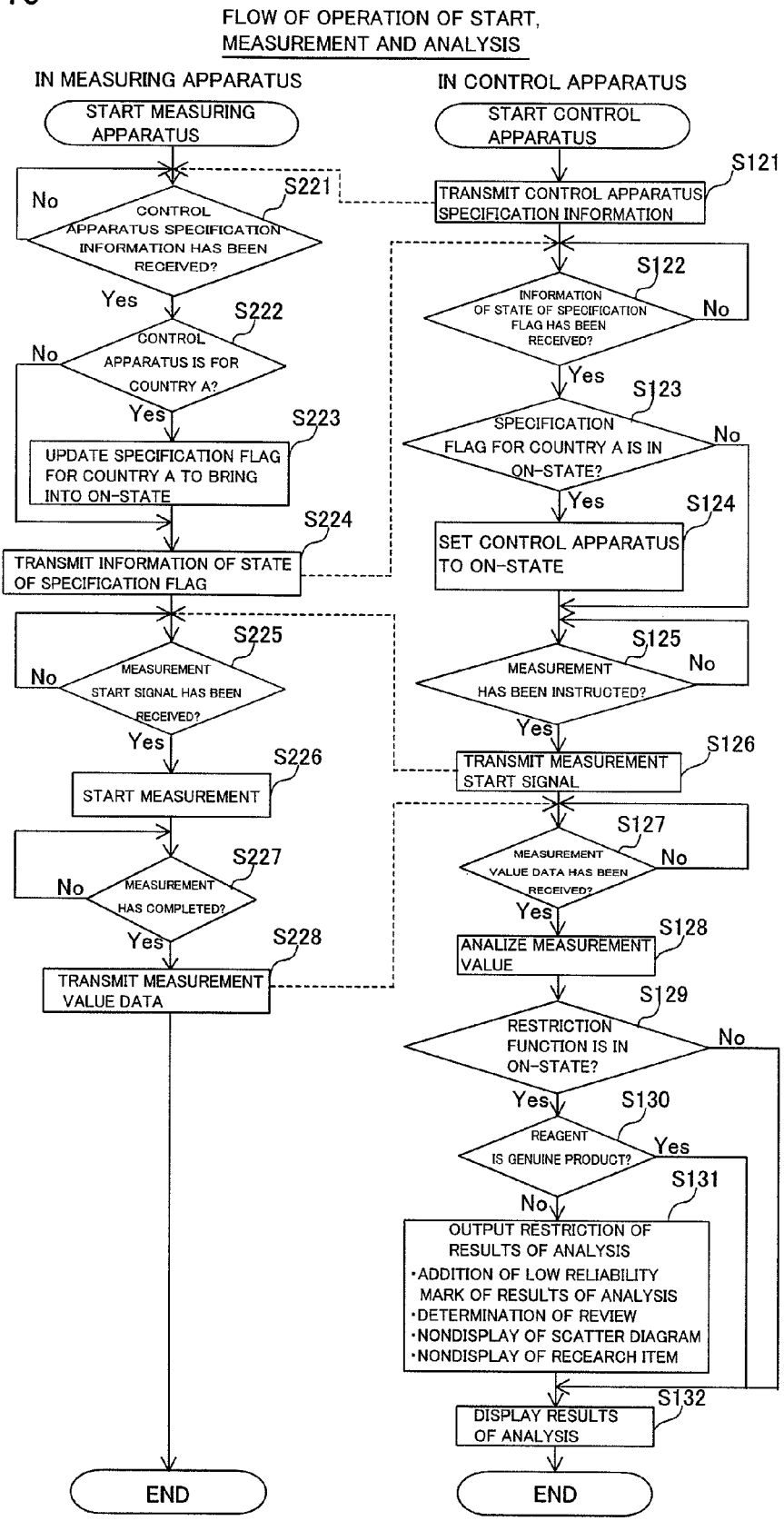
FIG. 10 is a flow chart for illustrating operations of start, measurement and analysis of the urinary particle analyzer according to the embodiment shown in FIG. 1.

According to this embodiment, when the user starts the measuring apparatus 2 and the application program 304a (305.a) installed into the control apparatus 3 is started, the CPU 301a transmits, to the measuring apparatus 2, the control apparatus specification information as to the country of the specification to which the control apparatus 3 is set at a step S121 in FIG. 10. At this time, a background of a screen to be displayed on the display section 302 is displayed in red when the user starts the application program 304a for country A, the background of the screen is displayed in blue when the user starts the application program 305a for the countries other than country A.

According to this embodiment, in the measuring apparatus 2, the CPU 208 determines whether or not the control apparatus specification information transmitted from the control apparatus 3 has been received at a step S221, and this determination is repeated until the control apparatus specification information is received. When the control apparatus specification information is received, the CPU 208 determines whether or not the control apparatus 3 is under the specification for country A on the basis of the received control apparatus specification information at a step S222. When the control apparatus 3 is under the specification for country A, the CPU 208 stores the information indicating the control apparatus 3 is under the specification for country A in the memory 211 such as BBURAM (battery backup RAM) at a step S223. More specifically, the CPU 208 updates to bring a specification flag for country A into an ON-state and the specification flag for country A is stored in the memory 211. According to this embodiment, this specification flag for country A is stored in the memory 211 so as to be unable to return to an OFF-state once the specification flag is updated to be brought into the ON-state. Therefore, when the application program 304a for country A is installed into the control apparatus 3, the specification flag for country A is set to the ON-state in the memory 211 of the measuring apparatus 2 and, then the ON-state of the specification flag for country A in the memory 211 is not returned to an OFF-state even when the application program 305a for the countries other than country A is installed into the control apparatus 3 in an overwrite manner. When the control apparatus 3 is under the specification for country B, country C or country D other than country A, the operation advances to a step S224 without updating to bring the specification flag for country A into the ON-state. At a step S224, the CPU 208 transmits the state information of the specification flag for country A from the measuring apparatus 2 to the control apparatus 3. In other words, information as to whether the specification flag for country A stored in the memory 211 of the measuring apparatus 2 is in the ON-state or the OFF-state is transmitted from the measuring apparatus 2 to the control apparatus 3.

In the control apparatus 3, the CPU 301a determines whether or not the state information of the specification flag for country A transmitted from the measuring apparatus 2 has been received at a step S122. This determination is repeated until specification flag state information is received. When the specification flag state information is received, the CPU 301a determines whether or not the specification flag for country A of the measuring apparatus 2 is in an ON-state at a step S123. When the specification flag for country A is in the ON-state, a restriction function is set to an ON-state in the application program 304a (305a) so as to activate particular restriction for country A described later at a step S124. Even when the application program 305a for the countries other than country A has started, the particular restriction function for country A is set to the ON-state at a step S124. In other words, the application program 304a for country A is first installed into the control apparatus 3 and the specification flag for country A of the measuring apparatus 2 is updated to be brought into the ON-state and the application program 305a for the countries other than country A is thereafter installed into the control apparatus 3 in an overwrite manner, for example, the particular restriction function for country A (output restriction function of the results of analysis) is activated although the control apparatus 3 is under the specification for country B, country C or country D. Further, once the application program 304a for country A is installed, the particular restriction function for country A (output restriction function of the results of analysis) is activated even when the application program 305a for the countries other than country A is started. In a case where the application program 304a for country A has never installed, the particular restriction function for country A (output restriction function of the results of analysis) is not activated when the application program 305a for the countries other than country A is started.

In the determination at the step S123, when the specification flag for country A of the measuring apparatus 2 is in an OFF-state, on the other hand, the CPU 301a determines whether or not an instruction of measurement start from the user has been made at a step S125. When the instruction of the measurement start is made, the CPU 301a transmits a signal of the measurement start to the measuring apparatus 2 at a step S126.

In the measuring apparatus 2, the CPU 208 determines whether or not the signal of the measurement start transmitted from the control apparatus 3 has been received at a step S225. When the signal is received, the measuring apparatus 2 starts measuring urinary particles at a step S226. Then, it is determined whether or not the measurement has been completed at a step S227. When the measurement is not completed, this determination is repeated while continuing the measurement. When the measurement has completed, measurement value data is transmitted to the control apparatus 3 through the LAN adapter 209 at a step S228 and the operation in the measuring apparatus 2 is ended.

In the control apparatus 3, the measurement value data transmitted from the measuring apparatus 2 is received at a step S127, and the measurement value processing (analysis processing) is performed on the basis of the received measurement value data at a step S128. Then the CPU 301a determines whether or not the particular restriction function for country A is set to an ON-state at a step S129, and the operation advances to a step S132 when the particular restriction function for country A is not in the ON-state. When the restriction function is in the ON-state, the CPU 301a determines whether or not the used reagent is the dedicated reagent (genuine product) on the basis of the state of the genuine product flag stored in the memory 211 at a step S130. When the used reagent is the dedicated reagent (genuine product), the analytical result screen (not shown) is displayed at a step S132 and the operation is ended.

Figure 11:
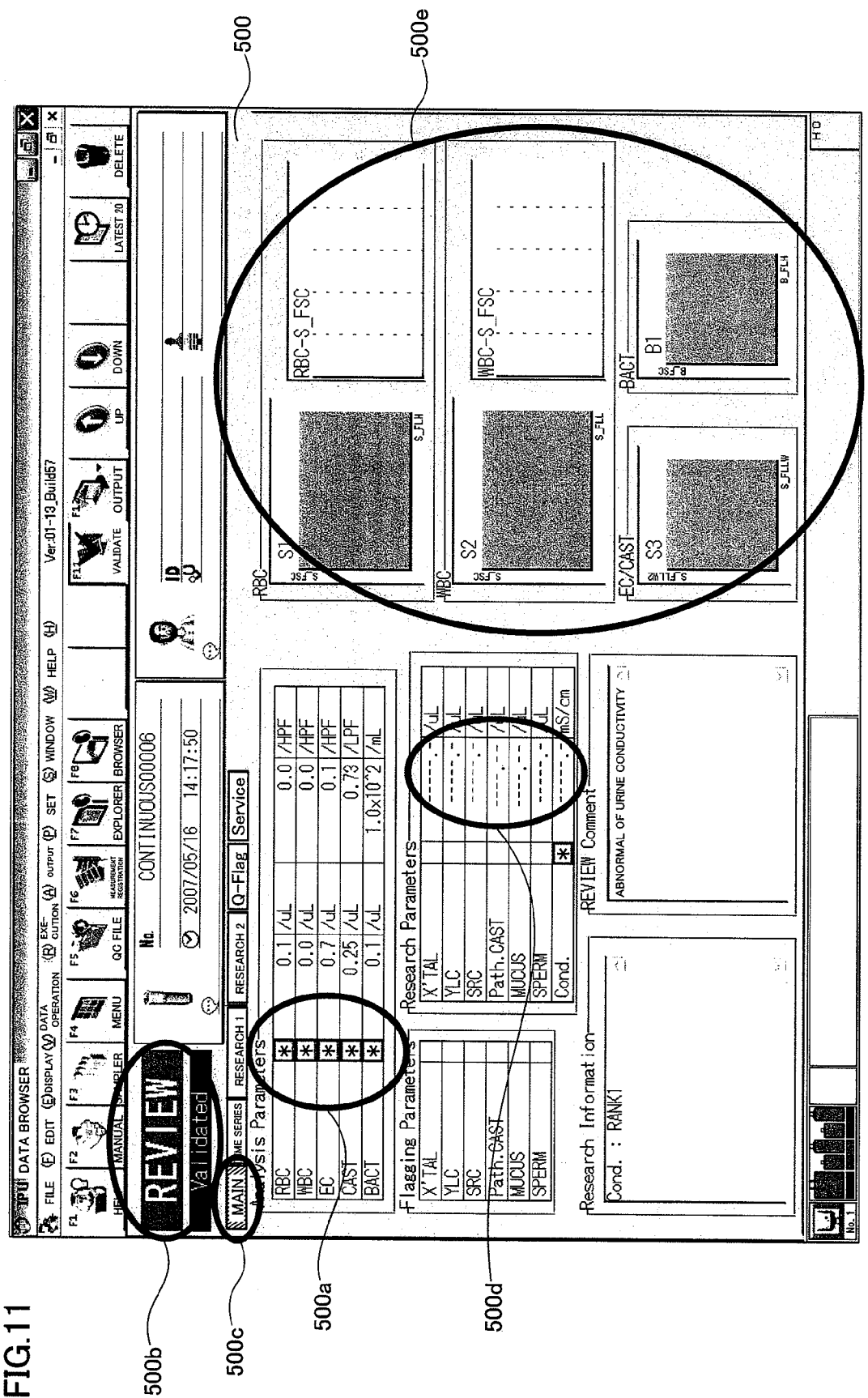
FIG. 11 is a diagram showing an analytical result screen of the urinary particle analyzer according to the embodiment shown in FIG. 1.

When the used reagent is the nondedicated reagent (non-genuine product), on the other hand, a partial function of a display program of the specimen analysis program included in the application program 304a (305a) is restricted on the basis of the restriction program at a step S131 to perform the output restriction of the results of analysis, and the analytical result screen 500 subjected to the output restriction is displayed on the display section 302 at a step S132. More specifically, asterisks (*) on a display region 500a are appended in columns of all of base items on the analytical result screen 500 in a state of selecting a main tab 500c as shown in FIG. 11. This indicates that reliability of the results of analysis is low because of the measurement by the nondedicated reagent (non-genuine product) and reexamination by a laboratory technician is desirable. A display region 500b at the upper left of the analytical result screen 500 is displayed in red for rendering REVIEW display prominent, so that the user can easily recognize reexamination is desired for the specimen. Since the reliability of the results of analysis is low, all numerical data regarding research items on a less important display region 500d is hidden by hyphens (-) and scatter diagrams of a display region 500e are also hidden. Thus, the possibility that the urinary particle analyzer 1 provides the user with the results of analysis having low reliability can be reduced as small as possible. According to this embodiment, the base items are items relating to RBC (red blood cells), WBC (white blood cells), EC (epithelial cells), CAST (casts) and BACT (bacteria), research items are items relating to X'TAL (crystals), YLC (yeast-like fungi), SRC (small round cell), Path. CAST (sickly cast including cell components), MUCUS (mucus fibril), SPERM (sperms) and Cond. (urine conductivity). According to this embodiment, operations at the steps S130 and S131 are operations by the particular restriction function for country A.

According to this embodiment, as hereinabove described, the CPU 301a formed so as to control the display section 302 to the specification for country A when the application program 304a for country A starts while controlling the display section 302 to the specification for the countries other than country A when the application program 305a for the countries other than country A starts is provided, whereby the single CPU 301a can perform control for different countries. In this urinary particle analyzer 1, the CPU 301a is so formed as to perform the particular control for country A on display section 302 even when the application program 305a for the countries other than country A starts in a case where the memory 211 stores the information indicating the control by the CPU 301a is for country A, whereby when the urinary particle analyzer 1 is used in country A, the control for country A can be performed even when the user starts the application program 305a for the countries other than country A so far as the memory 211 stores the information that the control by the CPU 301a is for country A. In other words, this urinary particle analyzer 1 can perform the control for country A at the time of use in country A, even when the application program 305a for the countries other than country A is started.

According to this embodiment, the CPU 301a controls the display section 302, so that the background of the screen is displayed in red when the application program 304a for country A is started, while the background of the screen is displayed in blue when the application program 305a for the countries other than country A is started, whereby the user can easily visibly confirm by the background color of the display section 302 which application program of the application program 304a for country A and the application program 305a for the countries other than country A is started.

According to this embodiment, the program controlling the display section 302 for country A and the program controlling the display section 302 for countries other than country A are preferably provided in the application program 305a for the countries other than country A, whereby the control for country A can be performed also in a case application program 305a for the countries other than country A is started even when the application program 304a for country A is uninstalled and deleted from the inside of control apparatus 3 so far as the memory 211 stores the information indicating the control by the CPU 301a is for country A.

According to this embodiment, the measuring apparatus 2 separated from the control apparatus 3 including the CPU 301a is provided with the memory 211, whereby the recorded contents of the memory 211 can be reliably preserved also when the control apparatus 3 is initialized (formatted) by the user and all of the recorded contents in the control apparatus 3 is deleted or also when the control apparatus 3 is replaced with another control apparatus. Thus, the control for country A can be reliably performed also when the application program 305a for countries (country B, country C and country D, for example) other than country A is started so far as the memory 211 stores the information indicating the control by the CPU 301a of the control apparatus is for country A.

Although the present invention has been described and illustrated in detail, it is clearly understood that the same is by way of illustration and example only and is not to be taken by way of limitation, the spirit and scope of the present invention being limited only by the terms of the appended claims.

For example, while the aforementioned embodiment of the present invention is applied to the urinary particle analyzer employed as an exemplary analyzer, the present invention is not restricted to this but the present invention may be applied to another specimen analyzer such as a multiple hemocyte analyzer, a blood coagulation measuring apparatus and an immunoanalyzer.

While the particular restriction for country A is the output restriction of the results of analysis displayed on the display section in the aforementioned embodiment, the present invention is not restricted to this but the restriction may be restriction for not measuring the research items in the measuring apparatus or restriction for not analyzing the research items in the control apparatus, for example.

While when the specification flag for country A of the measuring apparatus is in the ON-state, the specification of the control apparatus remains unchanged and only the particular restriction function for country A is set to the ON-state in the aforementioned embodiment, the present invention is not restricted to this but the specification of the control apparatus may be set to the specification for country A in addition of setting the particular restriction function for country A to the ON-state when the specification flag for country A of the measuring apparatus is in the ON-state.

While the application program for country A and the application program for countries other than country A has substantially the same contents of the application program in the aforementioned embodiment, the present invention is not restricted to this but these application programs may have the contents of the application program different from each other.

While the background is displayed in red when the application program 304a starts while the background is displayed in blue when the application program 305a starts in the aforementioned embodiment, the present invention is not restricted to this but the display section 302 is so controlled that a display mode in a case where the application program 304a starts and a display mode in a case where the application program 305a starts are different from each other. For example, a part of a window displayed on the display section or color of a title bar may be changed or display color may be changed by providing a display device such as LED on the control apparatus 3 in order to distinguish types of the application programs.

While the control is changed between country A and the countries other than country A in the aforementioned embodiment, the control may be changed between countries A and B and countries other than countries A and B. For example, it is determined that the control apparatus is not the specification for country A at the step S222 in FIG. 10 (NO at the step S222), and it is thereafter determined whether or not the control apparatus is for country B. When the control apparatus is for country B, the specification flag for country B is updated to be brought into an ON-state in the memory 207. Then the information indicating that the specification flag for country B is in the ON-state is transmitted at the step S224. Further, the CPU 301a in the control apparatus executes the results of analysis output restriction for country B at the step S131. According to this structure, the specification of the control apparatus can not be changed to the specification for countries other than countries A and B once the application program for country A is installed, and the specification of the control apparatus can not be changed to the specification for countries other than countries A and B once the application program for country B is installed.

While the control for country A is executed when the application program for country B or country D is installed and the application program for country A is thereafter installed in the aforementioned embodiment, the control for country B or country D first installed may be executed also when the application program for country B or country D is installed and the application program for country A is thereafter installed. For example, it is determined that the control apparatus is not the specification for country A at the step S222 in FIG. 10 (No at the step S222) and it is thereafter determined whether or not the control apparatus is for B country. When the control apparatus is for B country, the specification flag for country B is updated to be brought into the ON-state in the memory 207. Thereafter the ON-state of the specification flag for country B is not changed even when the application program for country A is installed. In other words, the specification flag for country A is simply not updated to be brought into the ON-state when the specification flag for country B is in the ON-state at the step S223.

What is claimed is:

1. An analyzer comprising:
a measurement apparatus for measuring a specimen and acquiring measurement data;
a controller configured to install at least one of a first application program and a second application program different from the first application program, and for analyzing the measurement data acquired by the measurement apparatus;
an output section for outputting an analysis result obtained by the controller; and
a memory,
wherein the first application program comprises a program for controlling, upon being executed by the controller, at least one of a measurement operation by the measurement apparatus, an analysis operation by the controller and an output operation by the outputting section in a first manner designed for a first area, the first application program further comprising a command to set a specification flag in the memory;
wherein the second application program comprises a program for selectively controlling, upon being executed by the controller, at least one of the measurement operation, the analysis operation and the output operation in the first manner or in a second manner according to the specification flag in the memory, the second manner being designed for a second area different from the first area;
wherein the controller:
sets the specification flag in the memory, and always controls at least one of the measurement operation, the analysis operation and the output operation in the first manner, when the first application program is installed and executed; and
controls at least one of the measurement operation, the analysis operation and the output operation in the second manner when the second application program is installed and executed before the first application program is installed and executed and the specification flag in the memory is not set.

2. The analyzer according to claim 1, wherein the specification flag in the memory is incapable of being reset.

3. The analyzer according to claim 2, wherein the memory is embedded in the measurement apparatus.

4. The analyzer according to claim 1, wherein the output operation comprises an operation of displaying a screen, and
a first screen displayed in the first manner is different from a second screen displayed in the second manner.

5. The analyzer according to claim 4, wherein the memory is embedded in the measurement apparatus.

6. The analyzer according to claim 4, wherein
the controller generates a result screen displaying an analysis result,
when the result screen is generated in the first manner and a predetermined condition is met, at least a part of the analysis result is masked in the result screen, and
when the result screen is generated in the first manner and the predetermined condition is not met, the analysis result is not masked in the result screen.

7. The analyzer according to claim 6, wherein the memory is embedded in the measurement apparatus.

8. The analyzer according to claim 1, wherein
the controller performs a specific process in the first manner, and
the controller skips the specific process in the second manner.

9. The analyzer according to claim 8, wherein the memory is embedded in the measurement apparatus.

10. The analyzer according to claim 8, wherein
the specific process includes a determination step of determining whether a reagent used by the measurement apparatus meets a predetermined condition, and
if the reagent does not meet the predetermined condition the controller imposes a limitation on at least one of the measurement operation, the analysis operation and the output operation.

11. The analyzer according to claim 10, wherein the memory is embedded in the measurement apparatus.

12. The analyzer according to claim 10, wherein
the limitation imposed on the output operation includes a masking of analysis result.

13. The analyzer according to claim 12, wherein the memory is embedded in the measurement apparatus.

14. The analyze according to claim 8, wherein
the specific process includes a determination step of determining whether a reagent used by the measurement apparatus meets a predetermined condition, and
if the reagent does not meet the predetermined condition the controller controls the output section to output the analysis result with an alert that the analysis result has a lower reliability than an analysis result obtained when the predetermined condition is met.

15. The analyzer according to claim 14, wherein the memory is embedded in the measurement apparatus.

16. The analyzer according to claim 1, wherein the memory is embedded in the measurement apparatus.

17. The analyzer according to claim 1, wherein the memory comprises a first memory and a second memory,
wherein the first memory is embedded in the measurement apparatus and the second memory is embedded in the controller, and
wherein the specification flag is set only in the first memory.

* * * * *